(12) United States Patent
Fleming, III

(10) Patent No.: US 6,673,060 B1
(45) Date of Patent: Jan. 6, 2004

(54) DRAINAGE CATHETER AND METHOD FOR FORMING SAME

(75) Inventor: James A. Fleming, III, Buffalo Grove, IL (US)

(73) Assignee: Manan Medical Products, Inc., Wheeling, IL (US)

( * ) Notice: Subject to any disclaimer, the term of this patent is extended or adjusted under 35 U.S.C. 154(b) by 0 days.

(21) Appl. No.: 09/557,665

(22) Filed: Apr. 25, 2000

(51) Int. Cl.$^7$ ................................. A61M 1/00
(52) U.S. Cl. .................. 604/540; 604/528; 604/544; 600/149
(58) Field of Search ................ 604/540, 541, 604/542, 543, 544, 528, 322, 326, 276, 532, 538; 600/146, 149; 264/563

(56) References Cited

U.S. PATENT DOCUMENTS

| | | | |
|---|---|---|---|
| 504,424 A | 9/1893 | De Pezzer | 604/104 |
| 1,207,479 A | 12/1916 | Bisgaard | 604/104 |
| 2,574,840 A | 11/1951 | Pieri et al. | 128/349 |
| 2,649,092 A | 8/1953 | Wallace | 128/349 |
| 3,924,633 A | 12/1975 | Cook et al. | 128/349 |
| 4,419,094 A | 12/1983 | Patel | 604/93 |
| 4,643,720 A | 2/1987 | Lanciano | 604/95 |
| 4,740,195 A | 4/1988 | Lanciano | 604/95 |
| 4,869,719 A | 9/1989 | Hogan | 604/174 |
| 4,963,129 A | 10/1990 | Rusch | 604/8 |
| 4,976,688 A | 12/1990 | Rosenblum | 604/95 |
| 5,041,085 A | 8/1991 | Osborne et al. | 604/51 |
| 5,213,575 A | 5/1993 | Scotti | 604/95 |
| 5,215,530 A | 6/1993 | Hogan | 604/174 |
| 5,275,151 A | 1/1994 | Shockey et al. | 128/4 |
| 5,352,198 A | 10/1994 | Goldenberg et al. | 604/95 |
| 5,368,564 A | 11/1994 | Savage | 604/95 |
| 5,383,852 A | 1/1995 | Stevens-Wright | 604/95 |
| 5,391,146 A | 2/1995 | That et al. | 604/95 |
| 5,397,304 A | 3/1995 | Truckai | 604/95 |
| 5,399,105 A | 3/1995 | Kaufman et al. | 439/609 |
| 5,399,165 A | 3/1995 | Paul, Jr. | 604/95 |
| 5,419,764 A | 5/1995 | Roll | 604/95 |
| 5,439,006 A | 8/1995 | Brennen et al. | 128/772 |
| 5,462,527 A | 10/1995 | Stevens-Wright et al. | 604/95 |
| 5,522,400 A | 6/1996 | Williams | 128/772 |
| 5,730,724 A | 3/1998 | Plishka et al. | 604/95 |
| 5,989,241 A | 11/1999 | Plishka et al. | 604/540 |
| 6,045,734 A * | 4/2000 | Luther et al. | 264/103 |

* cited by examiner

Primary Examiner—Edward K. Look
Assistant Examiner—Dwayne J. White
(74) Attorney, Agent, or Firm—Greenberg, Traurig, P.C.

(57) ABSTRACT

The present invention is directed to a drainage catheter including an elongated hollow drainage tube having a proximal end, a distal end, a tip, a flexible region adjacent the tip, a filament routing channel, a hub associated with the proximal end of the elongated hollow drainage tube, and a filament member associated with the flexible tip for altering the shape of the flexible tip to facilitate retention of the drainage tube in a patient's body. The filament member is slidably positioned within the filament routing member in the distal end of the drainage tube to permit removal of same from the catheter. The filament member exits the catheter through the hub, which further includes at least one filament member passageway. The filament member passageways enable slidable movement of the filament member therein, while also maintaining a liquid tight seal from leakage through the hub. Also disclosed is a method for manufacturing the drainage catheter including the steps of associating the filament member with an insert member, positioning the insert member and the filament member inside the distal end of the elongated hollow drainage tube, energizing the distal end of the elongated hollow drainage tube proximate the insert member to secure the insert member and filament within a filament routing channel in the elongated hollow drainage tube, and forming a hub on the proximal end of the elongated hollow drainage tube around the filament member to create a liquid tight seal.

38 Claims, 3 Drawing Sheets

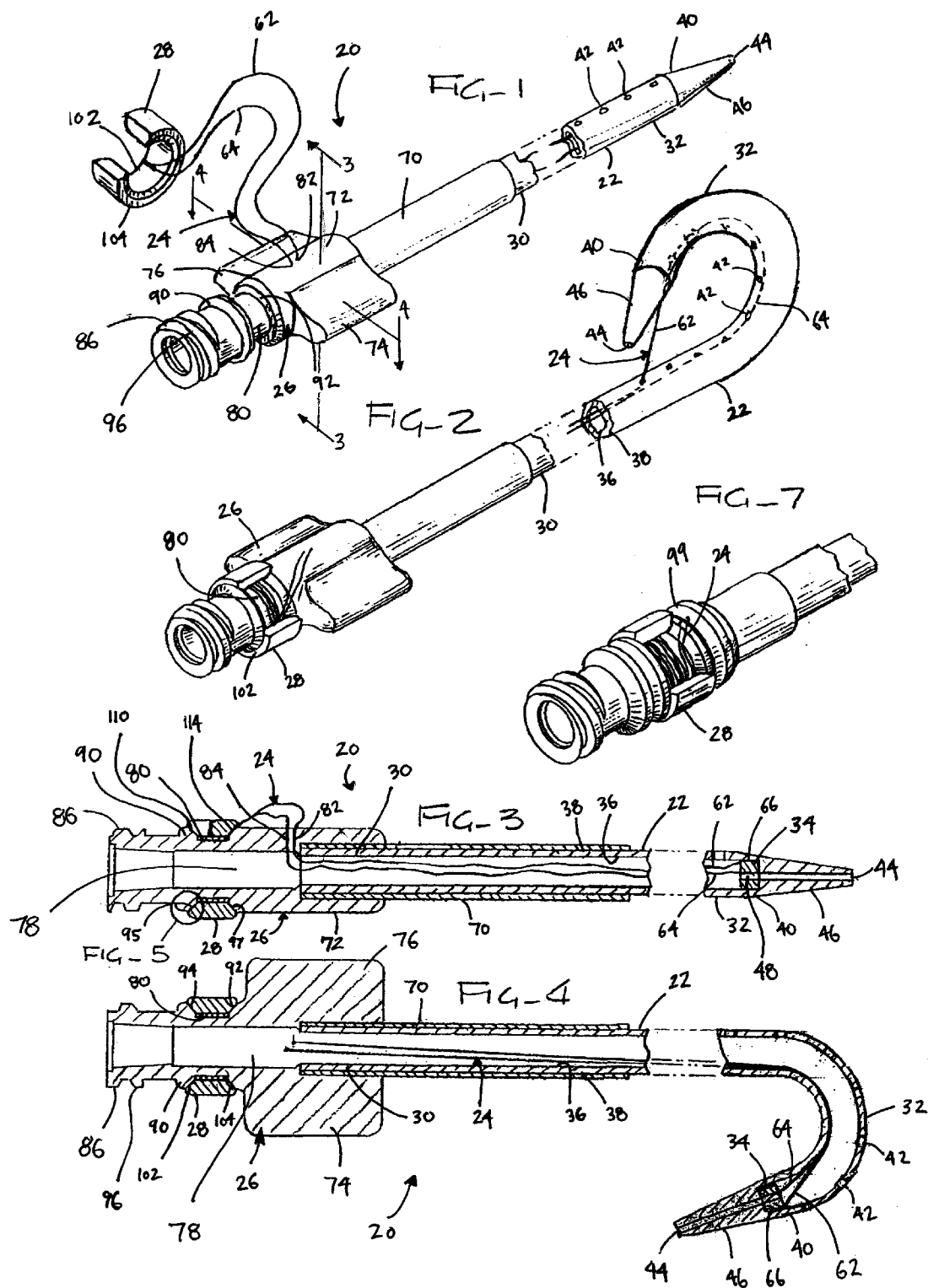

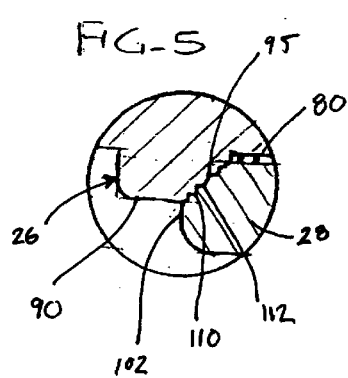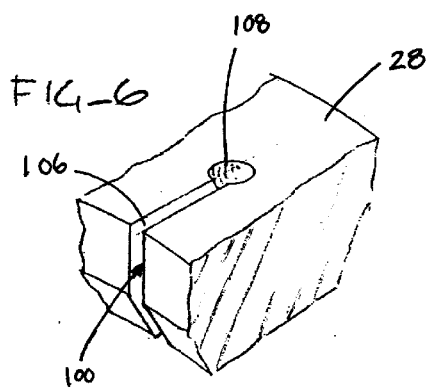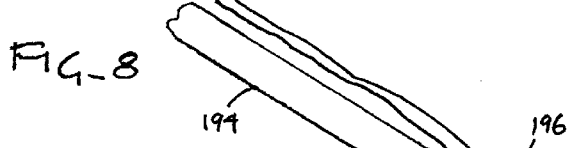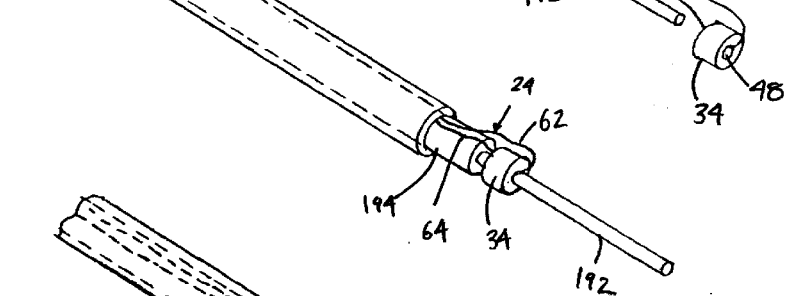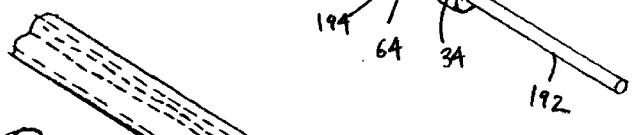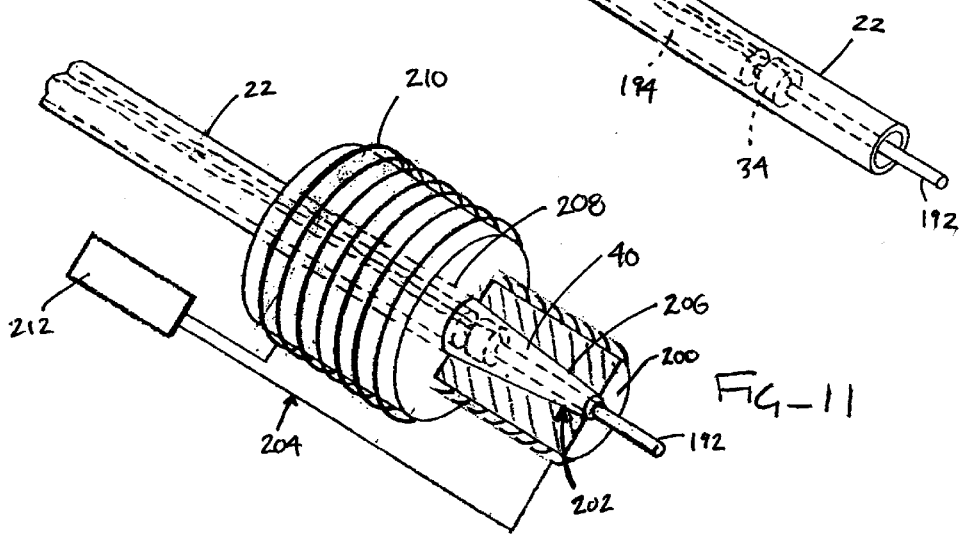

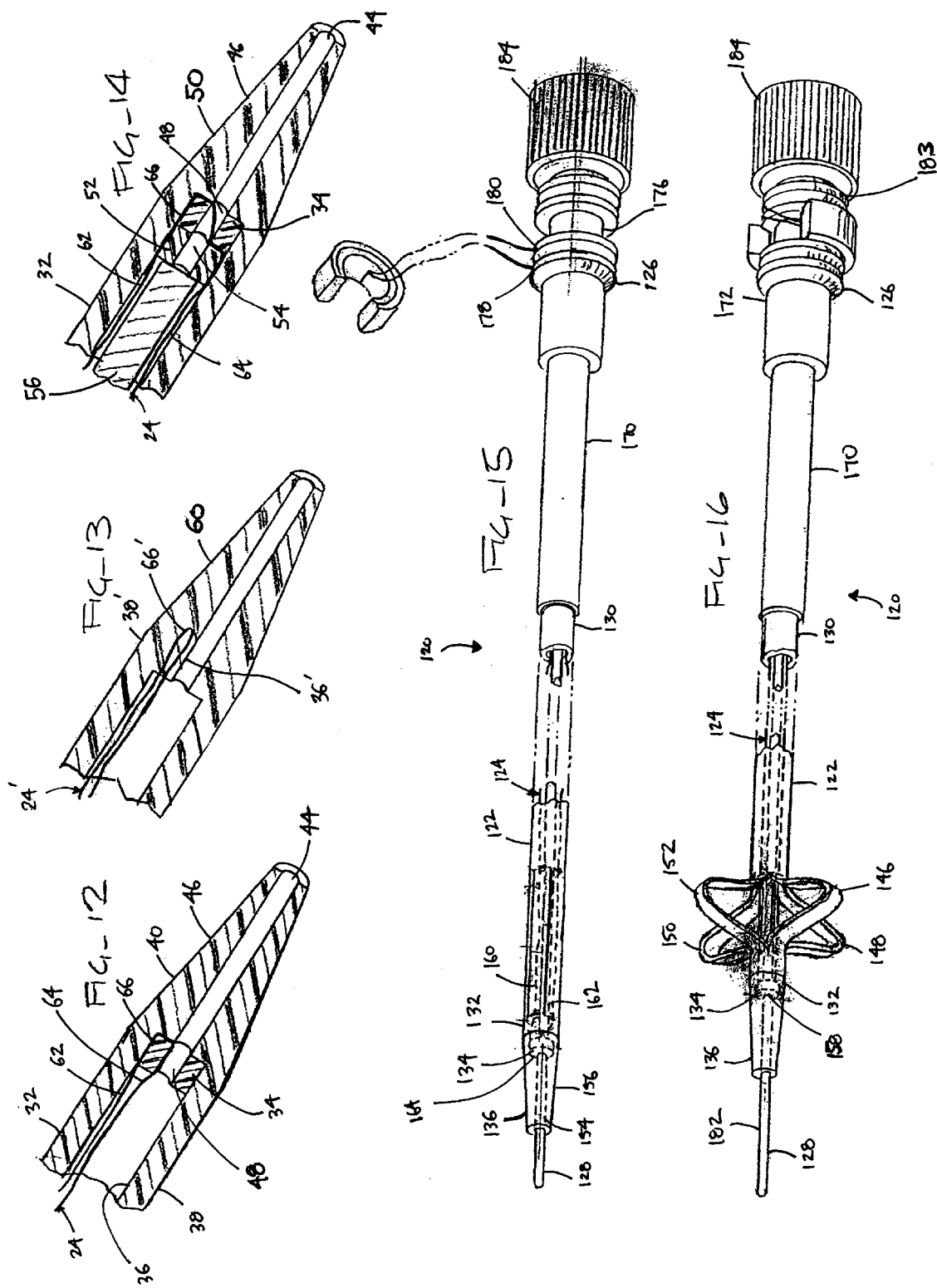

DRAINAGE CATHETER AND METHOD FOR FORMING SAME

BACKGROUND OF THE INVENTION

1. Field of the Invention

The present invention relates in general to drainage catheters and, more particularly, to a drainage catheter for draining fluid from a body cavity of a patient.

2. Background Art

Drainage catheters for draining fluid from a body cavity of a patient have been known in the art for many years. Indeed, the practice of inserting a drainage catheter into a body cavity has become a routine medical procedure. Generally, the catheter is inserted into the patient's body cavity with the aid of insertion tools, such as a needle or stiffening cannula. Once in position, the shape of the flexible tip at the end of the cavity is typically altered to maintain the tip within the cavity, and, in turn, to preclude inadvertent removal of the drainage catheter from the patient's body. Various ones of these locking catheters have been developed with the capacity to form J-shape, pigtail or other loops at their distal end. The loop is typically formed by retracting a flexible tensioning member, which extends from a distal end down the length of the catheter to a proximal end, where the tensioning member typically exits the catheter. The tensioning member is typically locked into place and sealed at the exit point by a retention member.

For instance, Goldenberg, et al., U.S. Pat. No. 5,352,198 discloses a locking catheter system wherein a tensioning member, in the form of a flexible suture, is capable of forming a loop in the distal end of the catheter. The suture extends through the catheter to the proximal end thereof, where it exits the catheter through a suture exit point. An annular latex sleeve covers the outer surface of the catheter near its proximal end to, in turn, cover the suture exit, thus helping to seal the catheter from leakage. Additionally, an annular silicone sleeve is then rolled over the latex sleeve to both secure the suture in a locked position, and to further minimize leakage.

Somewhat similarly, Paul, Jr., U.S. Pat. No. 5,399,165, discloses a lockable connector positioned near the proximal end of a drainage catheter to lock a tensioning string in place. The lockable connector includes a resilient sleeve having a channel for housing the string and a string exit port. The connector further includes a pivotably attached lever with a cam surface at its sealing end positioned adjacent the sleeve. Pivoting the lever compresses the sleeve, thus locking the tensioning string and the flexible tip in a desired loop orientation. Further, the lever functions to seal the string exit point in the catheter from leakage.

Likewise, Plishka, et al., U.S. Pat. No. 5,989,241, incorporated herein by reference, discloses a drainage catheter apparatus having a hub member through which a tensioning drawstring exits the catheter. The hub includes a sealing member constructed of elastomeric material to seal the drawstring opening and to automatically seal the passage of fluid therethrough, while also enabling extension of the flexible drawing member to lock the distal end of the catheter in a looped configuration.

While these and other devices have worked well for securing the tensioning member and thus the flexible tip in a specific looped orientation, fluid may leak from certain ones of these catheters at the point through which the flexible tensioning member exits the catheter. Moreover, many of these references require a separate member or assembly associated with the tensioning member exit point to seal the exit point from liquid leakage. These separate sealing assemblies are not only additional system components, but also mandate increased manufacturing and assembly time to form a catheter device.

Still other prior art locking catheters require threading of a string or flexible tensioning member through multiple openings in the distal end of the catheter, to form a loop which is suitable for coiling the distal end of the catheter. Typically, a portion of the string is threaded outside the distal end of the catheter to facilitate curling of the flexible tip by mere tensioning of the string. However, a looped threading pattern often requires considerable time and effort in the manufacturing process. In particular, the string must be extended from the proximal end, all the way through the catheter body, out the flexible tip, outside a portion of the distal end, back through the distal end, and back to the proximal end of the catheter. Moreover, if a full 360° loop is not required, such as in those situations where only a slight curl or a J-shaped curl is sufficient, a portion of the flexible tensioning member still remains outside of the catheter body. Exposed, the string is subject to severing.

Certain references, such as Pieri, et al., U.S. Pat. No. 2,574,840, and Wallace, U.S. Pat. No. 2,649,092, have sought to anchor the flexible tensioning member within the distal end of the catheter. For instance, the Pieri catheter includes a metal ring positioned in the distal end thereof for securing a tensioning string therein. The string may be pulled through an exit point in the proximal end of the catheter, thus either guiding or curling the tip of the catheter. Somewhat similarly, Wallace anchors a flexible member in the tip of a Malecot catheter. In particular, the flexible member is anchored in the tip of the catheter with a plug, which is permanently affixed therein. Upon tensioning of the string, the distal end of the catheter is pulled toward the proximal end of the catheter, thus extending winged ribs to form drainage openings for drainage of fluids from a body cavity.

While these catheters with an anchored tensioning member appear to be effective for certain applications, the tensioning member is permanently locked within the catheter. Thus, the tensioning member cannot be removed from the catheter, as is common practice before removing a catheter from a patient's body. It is desirable to remove the string to avoid severing of the string inside the patient's body or inadvertently retaining a portion or all of the string inside a patient's body.

Still other references have disclosed anchoring or securing a tensioning member or wire in the tip of a catheter to facilitate steering of the catheter through a patient's body, including Truckai, U.S. Pat. No. 5,397,304, That, et al, U.S. Pat. No. 5,391,146, Savage, U.S. Pat. No. 5,368,564, Stevens-Wright, U.S. Pat. No. 5,383,852 and Brennen, et al., U.S. Pat. No. 5,439,006. These references generally disclose steering catheters with a closed end for probing desired parts of a patient's body. Many of these catheters contain electrodes in a closed distal end to take readings or vital signs from the heart region of a patient's body.

While these catheters work well in a particular context, these catheters are not designed to drain body fluid from a patient. Specifically, the flow of body fluid through an electrode containing flexible tip may damage the ability of the catheter to perform its intended function. Additionally, the steering wire is often permanently anchored in the flexible tip at multiple points, and thus not intended to be removed from those catheters.

Thus, it is desired to provide a drainage catheter which contains a tensioning member exit point which is liquid tight both during curling of the flexible tip and after curling of the flexible tip. Furthermore, it is desired to provide a liquid-tight seal without additional sleeves, assemblies or other catheter components.

It is further desired to provide a drainage catheter wherein the tensioning member is retained directly in the tip of the drainage catheter to facilitate manufacturing of the drainage catheter, while still permitting complete removal of the tensioning member from the drainage catheter before removing the catheter from a patient's body.

It is also desired to provide a drainage catheter which is relatively easier and less expensive to manufacture, while solving the other needs in the art described above. Particularly, it is desired to provide a method of manufacture of drainage catheter wherein the filament member is molded into the flexible tip. It is also desired to provide a method of manufacturing a drainage catheter to reduce the amount of time and effort in threading a tensioning member within a locking drainage catheter to allow substantial looping of the flexible tip.

These and other objects of the present invention will become apparent in light of the present specification, claims and drawings.

SUMMARY OF THE INVENTION

The present invention is directed to a drainage catheter comprising an elongated hollow drainage tube having a proximal end, a distal end, a tip and a flexible region adjacent the tip, a filament routing channel, a hub associated with the proximal end of the elongated hollow drainage tube, and a filament member associated with the distal end for altering the shape of the flexible region to facilitate retention of the drainage tube in a patient's body. The filament member is preferably slidably positioned within the filament routing channel in the distal end of the drainage tube to permit removal of the filament member from the catheter.

In one embodiment, the drainage catheter further includes an insert member which is formed into the distal end of the elongated hollow drainage tube to form the filament routing channel. In one embodiment, the insert member is preferably constructed from a plastic of a higher durometer than that forming the elongated hollow drainage tube, yet which is still chemically bonded and/or fused to the inside of the drainage tube. In another embodiment, the insert member is formed of the same material as the drainage tube, thus melt-flowing into the outer drainage tube. In yet another embodiment, the insert member is formed from a material distinct from the drainage tube, such as stainless steel.

In another embodiment, the drainage catheter is formed with a second insert member to alter the orientation of the filament member in the distal end of the elongated hollow drainage tube.

In yet another embodiment, the filament member remains inside the elongated hollow drainage tube until exiting through the hub. In a contrasting embodiment, the filament member extends outside at least a portion of the drainage tube to facilitate alteration of the shape of the distal end of the drainage tube.

The filament member preferably exits the catheter through the hub, which further includes at least one filament member passageway. The at least one filament member passageway enables slidable movement of the filament member therein, while also maintaining a liquid tight seal substantially precluding leakage through the hub.

The present invention also addresses a method for manufacturing the drainage catheter including the steps of positioning the filament member inside the distal end of the elongated hollow drainage tube, energizing the distal end of the elongated hollow drainage tube to form a filament routing channel positioned within the distal end such that the filament member is positioned within and slidably routed through said filament routing channel, running the filament member through at least a portion of said elongated hollow drainage tube such that the filament member emanates from the proximal end of the drainage tube, and forming a hub on the proximal end of said elongated hollow drainage tube.

In one embodiment, the method further includes the step of associating the filament member with the insert member occurs before the step of positioning the filament member inside said distal end of the elongated hollow drainage tube. To this end, the step of positioning the filament member inside the distal end of the elongated hollow drainage tube further includes orienting the insert member and the filament member inside the distal end of the elongated hollow drainage tube.

In another embodiment, the step of orienting the insert member and the filament member inside the distal end of the elongated hollow drainage tube provides the filament member with an orientation relative to the inside surface of the elongated hollow drainage tube, and wherein the method further includes the step of positioning the filament member relative to a second insert member inside the distal end of the elongated hollow drainage tube to alter the orientation of the filament member relative to the inside surface of the elongated hollow drainage tube.

In yet another embodiment, the step of positioning the insert member and filament member inside the distal end of the elongated hollow drainage tube further includes the steps of positioning the insert member on a smaller diameter portion of a mandrel which includes a smaller diameter portion and a larger diameter portion, placing the elongated hollow drainage tube over the insert member and the filament member such that the insert member is inside the distal end of the elongated hollow drainage tube and such that the filament member runs inside the elongated hollow drainage tube.

In yet another embodiment, the method for forming a drainage catheter further includes the step of forming the distal end of the elongated hollow drainage tube to a desired shape, and which step preferably further includes inserting the distal end of the elongated hollow drainage tube into a die.

In another embodiment, the step of forming a hub onto the proximal end of the elongated hollow drainage tube includes forming the hub directly around the filament member, thereby creating at least one filament member passageway extending through the hub to house the filament member, and to permit slidable movement of the filament member through the hub. Preferably, the formation of the hub around the filament member renders the hub substantially liquid tight to prevent leakage of fluids from the drainage passageway of the hub through the filament member passageways.

BRIEF DESCRIPTION OF THE DRAWINGS

FIG. 1 is a perspective view of the drainage catheter according to the present invention;

FIG. 2 is a perspective view of the drainage catheter as shown in FIG. 1, but with a portion of the filament member extending outside the distal end to lock the flexible region in a coiled orientation;

FIG. 3 is a side elevational view in cross-section of the drainage catheter shown in FIG. 1, taken along lines 3—3;

FIG. 4 is a top elevational view in cross-section of the drainage catheter as shown in FIG. 1 with the flexible region in a curled orientation, taken along lines 4—4;

FIG. 5 is a side elevational view shown in cross-section of a portion of the drainage catheter as shown in FIG. 3;

FIG. 6 is a fragmentary perspective view of a portion of the securing member of the drainage catheter as shown in FIG. 1;

FIG. 7 is a perspective view of the drainage catheter according to another embodiment of the invention;

FIG. 8 is a perspective view of the mandrel, insert member and filament member used in manufacturing the drainage catheter of the present invention;

FIG. 9 is a perspective view of the elongated hollow drainage tube being positioned on the mandrel relative to the filament member and insert member according to the present invention;

FIG. 10 is a perspective view of the elongated hollow drainage tube being further positioned on the mandrel relative to the filament member and insert member according to the present invention;

FIG. 11 is a perspective view of the formation of the tip of the drainage catheter according to the present invention;

FIG. 12 is a side elevational view in cross-section of the tip of the drainage catheter shown in FIG. 1;

FIG. 13 is a side elevational view in cross-section of the tip of the drainage catheter according to another embodiment of the present invention;

FIG. 14 is side elevational view in cross-section of the tip according to still another embodiment of the present invention;

FIG. 15 is a perspective view of a Malecot drainage catheter according to the present invention; and FIG. 16 is a perspective view of the Malecot catheter shown in FIG. 13 with the tip in a retracted orientation.

DETAILED DESCRIPTION OF THE INVENTION

While this invention is susceptible of embodiment in many different forms, there are shown in the drawings and will herein be described in detail, several specific embodiments with the understanding that the present disclose is to be considered as an exemplification of the principals of the invention and is not intended to limit the invention to the embodiments illustrated.

Drainage catheter 20 is shown in FIGS. 1–6 as comprising elongated hollow drainage tube 22, filament member 24, hub 26 and securing member 28. At the outset, drainage catheter 20 will be shown and described as a locking-type catheter wherein a flexible tensioning member affirmatively alters the shape of the flexible tip of the drainage catheter to retain the same inside the body cavity of a patient. However, it is likewise contemplated that the distal end of the drainage catheter may be at least partially pre-formed or pre-altered to facilitate alteration of the tip to a looped, curled, coiled or other desired orientation. Of course, if the distal end of the drainage catheter is pre-formed, a stiffening cannula is preferably used for insertion of the drainage catheter into a patient's body, as is well known in the art and described below. Throughout this detailed description, like reference numerals will be used to designate like parts.

Elongated hollow drainage tube 22, shown in FIGS. 1–4, comprises proximal end 30, distal end 32, insert member 34, inner tube wall surface 36 and outer tube wall surface 38. Elongated hollow drainage tube 22 is preferably flexible to facilitate manipulation of the elongated hollow drainage tube within a patient's body. To this end, elongated hollow drainage tube 22 is preferably formed from a plastic and/or polymer, preferably polyurethane sold under the trade name Tecoflex. The elongated hollow drainage tube must be durable and non-reactive to bodily fluids coming into contact with the drainage tube, while at the same time remaining malleable and flexible to a accommodate a patient's cavities, passageways and movements.

Distal end 32, shown in FIGS. 1–4 and 14, includes flexible tip 40, drainage openings 42 and filament routing channel 66. While the actual tip of the drainage catheter need not be flexible, the general tip region is preferably flexible to facilitate alteration thereof. Thus, the tip will be referred to as a flexible tip throughout the specification. Flexible tip 40 further includes fluid opening 44 at the distal end of conical portion 46. Fluid opening 44 extends through conical portion 46 of flexible tip 40 so as to be in fluid communication with the inside of elongated hollow drainage tube 22. Flexible tip 40 is preferably capable of being altered to any number of orientations, including a J-curl (FIG. 4), pigtail loop (FIG. 2), 360° coil, or other orientations as would be known by those of ordinary skill in the art with the present disclosure before them. Of course, the degree of curl is dependent on construction and orientation of drainage catheter 20, including the specific threading pattern of filament member 24, the amount of tension placed on filament member 24, the length of elongated hollow drainage tube 22, the flexibility of the catheter material, etc. Moreover, while flexible tip 40 is shown in the drawings as having a conical shape to facilitate insertion of the drainage catheter into a patient's body, the tip may take any shape as would be known by those of ordinary skill in the art with the present disclosure before them.

Fluid from a patient's body cavity flows through opening 44 and drainage openings 42 into elongated hollow drainage tube 22 upon insertion of drainage catheter 20 into a patient's body cavity. While drainage openings 42 are shown as small holes drilled into one side of elongated hollow drainage tube 22, it is likewise contemplated that distal end 32 may include fewer or more drainage openings, even to the point of perforation. Drainage openings 42 are of a size and diameter to facilitate flow of fluids from a patient's body cavity, as known by those with ordinary skill in the art with the present disclosure before them. Accordingly, the size of drainage openings 42 may be altered to accommodate a specific drainage application. Further, while drainage openings 42 serve to facilitate drainage of fluid from a patient's body cavity, drainage openings 42 may also function to provide a threading hole for filament member 24, as will be described below. Of course, if fluid opening 44 in flexible tip 40 is sufficient to drain fluid from a patient's body cavity, drainage openings 42 may be unnecessary.

Filament routing channel 66 is shown in FIGS. 3, 4 and 12 as being positioned between insert member 34 and inner tube wall surface 36. As is described below, filament routing channel 66 is formed upon positioning and forming of insert member 34 into distal end 32 of elongated hollow drainage tube 22. Thus, filament routing channel 66 is preferably formed around filament member 24. However, filament routing channel 66 is of a sufficient diameter to permit slidable movement of filament member 24 therethrough. To this end, filament member 24 is of a higher melting point than at least one of elongated hollow drainage tube 22 and insert member 34, such that a portion of one or both of the drainage tube and the insert member preferably melt flows around at least a portion of the filament member.

Insert member 34 is shown in FIGS. 3, 4 and 14 as comprising an annular ring with opening 48. Insert member 34 is preferably also constructed of a polymer plastic, preferably also a polyurethane sold under the name Tecoflex, but is preferably harder than the elongated hollow drainage tube 22. Specifically, insert member 34 is preferably constructed of a higher durometer plastic than the plastic which forms elongated hollow drainage tube 22. Thus, while not necessarily the same material, insert member 34 is preferably formed from the same family of materials as is elongated hollow drainage tube 22, such that insert member 34 will bond to elongated hollow drainage tube 22 upon application of sufficient heat. In particular, it is preferable that insert member melt flows into or chemically bonds with elongated hollow drainage tube 22 during the formation of distal end 32 and flexible tip 40. [At the same time, insert member 34 is preferably of a stronger material so as to increase the integrity of filament routing channel 66, and to provide a secure anchor in distal end 32 for filament member 24 to slide around and/or through.

However, it is likewise contemplated that insert member may be formed from the same material as elongated hollow drainage tube 22. In this particular instance, insert member 34 and elongated hollow drainage tube 22 will share the same melting point, thus likewise permitting insert member 34 to be bonded directly into flexible tip 40 during the formation and shaping of flexible tip 40. In such a construction, insert member 34 still provides filament routing channel 66 and a secure anchor for filament member 24 to slide around and/or through.

It is also contemplated that insert member 34 may be constructed from a completely different material than elongated hollow drainage tube 22, such as stainless steel, other polymers or plastics or other metallic alloys. With an insert member 34 that does not chemically bond to elongated hollow drainage tube 22, the insert member may be molded inside flexible tip 40 during formation of the flexible tip. Additionally, the use of stainless steel or other metallic alloys in construction of insert member 34 may allow the insert member to also function as a radiopaque marker for use under x-ray or fluoroscopy. Of course, elongated hollow drainage tube 22 may also include such a marking element, or may likewise be treated with a different marker, such as barium sulfate.

Opening 48 in insert member 34, as shown in FIGS. 3, 4, 8–11 and 12, permits threading of filament member 24 through the insert member prior to placement of insert member 34 into flexible tip 40, and prior to formation of the flexible tip. Moreover, upon formation of flexible tip 40, opening 48 permits drainage of fluids from a body cavity through fluid opening 44, through flexible tip 40 and into elongated hollow drainage tube 22. Thus, the number of drainage openings may be minimized, or completely eliminated altogether, depending on catheter application. However, it is likewise contemplated that insert member 34 may take the form of a substantially solid plug (not shown in the drawings) which likewise acts as an attachment and anchor point for filament member 24. With such a construction, it is preferred that filament member 24 is molded directly into insert member 34. A solid insert member would mandate drainage openings in elongated hollow drainage tube 22, such as drainage openings 42 shown in FIGS. 1 and 2, to facilitate drainage of bodily fluids through the elongated hollow drainage tube.

Filament member 24 is shown in FIGS. 1–14 as comprising first segment 62 and second segment 64. As can be seen from FIGS. 8–11, filament member 24 is preferably threaded through insert member 34 prior to formation of distal end 32 of elongated hollow drainage tube 22 of drainage catheter 20. Filament member 24 is preferably constructed from a nylon mono-filament line; however, those of ordinary skill in the art with the present disclosure before will appreciate that filament member 24 may likewise be made from wire, stainless steel, plastic or other polymers to accomplish the same function. Of course, filament member 24 is preferably flexible to allow tensioning and de-tensioning thereof, while at the same time also preferably non-elongating to prevent longitudinal stretching of the filament member.

As can be seen FIGS. 1–6 and 12, first segment 62 of filament member 24 extends through one end of filament routing channel 66, down elongated hollow drainage tube 22 and out hub 26, while second segment 64 extends through the other end of filament routing channel 66, through opening 48 in insert member 34, and likewise down elongated hollow drainage tube 22 and out hub 26. Notably, while filament member 24 is retained in filament routing channel 66 in flexible tip 40 by insert member 34, filament member 24 remains slidable in filament routing channel 66 relative to both the insert member and the flexible tip. Thus, pulling first segment 62 shortens second segment 64, and vice versa. This slidable relationship permits either first segment 62 or second segment 64 to be severed, and for the entire filament member to be pulled around and/or through insert member 34, out elongated hollow drainage tube 22, and out of hub 26. This slidability feature is particularly advantageous in the drainage catheter context as it is common and often necessary to remove filament member 24 from drainage catheter 20 before removing drainage catheter 20 from a patient's body. Indeed, removal of filament member 24 precludes the inadvertent loss of any portion of filament member 24 in a patient's body.

In another embodiment, shown in FIG. 13, flexible tip 60 is shown having filament member 24' molded directly therein. In particular, filament routing channel 66' is created by molding filament member 24' directly into flexible tip 60 between inner tube wall surface 36' and outer tube wall surface 38'. Notably, this structure may also be formed by molding an insert member made of the same material as the elongated hollow drainage tube 22.

In yet another embodiment, shown in FIG. 14, flexible tip 50 includes second insert member 52. Second insert member 52 preferably includes opening 54, which aligns with opening 48 in insert member 34. Second insert member 52 is preferably constructed from the same material as insert member 34, preferably a higher durometer plastic than elongated hollow drainage tube 22. However, as with insert member 34, second insert member 52 may likewise be constructed from the same material, or completely different material such as steel, other polymers or other metallic alloys.

Second insert member 52 acts to alter the orientation of filament member 24 within flexible tip. In particular, and as is illustrated by comparing FIG. 12 with FIG. 14, insert member 34 causes first filament member segment 62 to extend along inner tube wall surface 36 in filament routing channel 66, while second segment 64 extends through opening 48 and, at least initially, into the middle of distal end 32 of elongated hollow drainage tube 22 in a first orientation. However, when second insert member 52 is formed into flexible tip 40, the orientation of filament member 24 is changed such that second segment 64 runs along an opposing portion of inner tube wall surface 36 from first segment 62. Altering of the attachment orientation of filament member 24 may be particularly advantageous in those applications where a stiffening cannula 56, shown in FIG. 14, is required for insertion of the drainage catheter into a patient's body. Specifically, the first and second segments of filament member 24 are much less likely to be inadvertently severed by stiffening cannula 56 as the stiffening cannula is positioned into the elongated hollow drainage tube 22 and up against second insert member 52. Of course, the stiffening cannula shown in FIG. 14 is just one example of a stiffening member for use in inserting a drainage catheter into a patient's body. It will be appreciated that stiffening cannula may include a smaller diameter portion extending through the insert members and out of the flexible tip, may have a sharpened tip end for assisting insertion into a patient's body cavity, may include both a hollow outer cannula and an inner sharpened stylet, or may take other configurations as would be known by those of ordinary skill in the art with the present disclosure before them.

Notably, and is shown in FIGS. 1, 3 and 4, filament member 24 may remain entirely inside elongated hollow drainage tube 22 until filament member 24 exits hub 26. Retracting filament member 24 through hub 26 alters the shape of flexible tip 40 to a J-shaped orientation which permits drainage catheter 20 to be retained within a patient's body. However, and is shown in FIG. 2, filament member 24 may also be threaded out of elongated hollow drainage tube 22, along outer tube wall surface 38, and back into elongated hollow drainage tube 22 at another point, as is conventionally known in the art. Such a threading of filament member 24 permits enhanced curling of flexible tip 40, such as the pigtail curl shown in FIG. 2. Those with ordinary skill in the art with the present disclosure before them will readily appreciate that any curl is possible depending upon the threading pattern of the filament member through elongated hollow drainage tube 22. Furthermore, while drainage openings 42 are shown as the exits and entrance points for filament member 24, it is likewise contemplated that filament member may exit and reenter elongated drainage tube 22 at different entrance and exit points.

Hub 26 is shown in FIGS. 1–5 as comprising annular sleeve 70, barrel portion 72, wings 74 and 76, drainage passageway 78, filament accepting region 80, filament member passageways 82 and 84 and connection region 86. As is shown in FIGS. 1–4, annular sleeve 70 is positioned over proximal end 30 of elongated hollow drainage tube 22 to facilitate formation of a liquid tight seal between hub 26 and elongated hollow drainage tube 22. While the remainder of hub 26 is preferably formed from a harder polyurethane plastic material, sleeve 70 is preferably of a flexible material, to permit flexible movement of sleeve 70 with elongated hollow drainage tube 22. However, it is likewise contemplated that sleeve may be constructed of a harder plastic material, such as the plastic from which barrel portion 72 is formed. Likewise, elongated hollow drainage tube 22 may be directly connected to hub 26, without any intervening sleeve.

Barrel portion 72 defines drainage passageway 78. Wings 74 and 76 extend outwardly from barrel portion 72, and provide an enhanced gripping and manipulating structure for drainage catheter 20. Barrel portion 72 is preferably constructed from a plastic material, preferably of a higher durometer and higher strength than elongated hollow drainage tube 22. Indeed, inasmuch as hub 26 never enters a patient's body, it need not be flexible for manipulation inside a patient.

Filament accepting region 80, shown in FIGS. 1–5, includes collar 90, which in combination with barrel portion 72 of hub 26, provides a spool for filament member 24. Collar 90 preferably further includes a beveled face 94, which opposes beveled face 92 on barrel portion 72. As will be described below, beveled surfaces 92 and 94 mirror those found on securing member 28 to facilitate locking securing member 28 into place, and thus locking flexible tip 40 into a particular altered configuration. Additionally, beveled face 94 on flange 90 and beveled face 92 on barrel portion 72 further include gripping surfaces 95 and 97, respectively. Gripping surface 95 is shown in FIG. 5 as comprising mating teeth for mating engagement with like surfaces on securing member 28. However, gripping surfaces 95 and 97 may likewise comprise other ratcheting teeth configurations, roughened finish, dimpled surface or any other gripping surface as would be known by those of ordinary skill in the art with the present invention before them.

Filament member passageways 82 and 84, shown in FIG. 3, permit filament member 24 to exit from the inside of elongated hollow drainage tube 22 and drainage passageway 78, and out hub 26. Filament member passageways 82 and 84 are preferably formed only upon molding of hub 26 around first segment 62 and second segment 64 of filament member 24. Thus, filament member passageways 82 and 84 have a dimension which is only slightly larger than the peripheral shape of the first and second segments of filament member 24. Inasmuch as hub 26 is preferably formed from a polyurethane plastic, hub 26 at least partially shrinks upon cooling. Shrinkage of hub 26 around first segment 62 and second segment 64 of filament member 24 provides a liquid tight seal between drainage passageway 78 and the outer environment. Inasmuch as filament member 24 has a higher melting point than hub 26 and thus does not melt into hub 26, first segment 62 and second segment 64 remain slidable within filament member passageways 82 and 84. That sliding capacity allows filament member 24 to be tensioned, and to shape flexible tip 40 into a desired orientation. Moreover, there is no additional sealing member or sleeve necessary for the outer or inner portion of hub proximate the entrance or exit points of filament member 24.

Connection region 86, shown in FIGS. 1–4, may be used to connect drainage catheter 20 to a desired structure, such as a drainage outlet or a stiffening cannula, such as that shown in FIGS. 15 and 16. To this end, connection region 86 may further include threads 96, to accept a pair of mating threads on a mating surface.

Inasmuch as filament member 24 is molded directly into the hub, the hub may take any shape, such as hub 99 shown in FIG. 7. The hub can be molded to any number of shapes around filament member 24 to form a fluid tight passageway through which filament member 24 readily slides.

Securing member 28, shown in FIGS. 1–7, comprises filament receiving region 100, first surface 102 and second surface 104. Filament receiving region 100 includes slot 106 and depression 108. First segment 62 and second segment 64 of filament member 24 are preferably tied in a knot at their open ends, which knot is preferably positioned into slot 106, and eventually into depression 108. Depression 108 locks the filament member knot into place, and an epoxy or other sealant may be used to firmly secure filament member 24 into securing member 28.

First surface 102 of securing member further includes beveled portion 110, while second surface 104 includes beveled portion 114. As discussed above, the beveled portions of securing member 28 fit into and mate with beveled surfaces 90 and 92 on filament accepting region 80 of hub 26. Further, beveled portion 110 preferably includes gripping surface 112, while beveled portion 114 may also include a gripping surface to enhance the secured relationship between securing member 28 and hub 26. As discussed above, those gripping surfaces may take any number of forms, including gripping teeth, ratchet teeth, roughened surface, dimples, depressions, etc.

Further, as can be seen from the drawings, securing member 28 is preferably C-shaped member to permit easy attachment to and detachment from filament accepting region of hub 80. Securing member 28 simply snaps on to hub 26. Of course, the beveled surfaces of securing member 28 permit a wide range of filament member 24 thicknesses to be wound on filament accepting region 80 of hub 26. As can be seen, securing member 28 locks over the top of the wound member filament to secure same in a tensioning orientation. Positioning securing member 28 in a locked orientation, in turn, locks flexible tip 40 in a desired altered orientation.

In operation, drainage catheter 20 is inserted into a patient's body cavity. This step may be performed with the aid of a stiffening cannula, which is inserted into and through hub 26 and into elongated hollow drainage tube 22. The stiffening cannula, such as that shown in FIGS. 15 and 16, may also be attached to connecting region 86 of hub 26, to both ensure a secure relationship between the stiffening cannula and the drainage catheter and to prevent premature fluid flow out of the drainage catheter. Once inside a body cavity, fluid enters elongated hollow drainage tube 22 through fluid opening 44 in flexible tip 40, as well as through drainage openings 42. However, inasmuch as first segment 62 and second segment 64 of filament member 24 are slidably retained in filament member passageway 82 and 84 in hub 26, fluid does not prematurely leak through the hub, but instead exits the hub only upon opening of drainage passageway 78.

Upon proper catheter positioning, the portions of first segment 62 and second segment 64 extending out of hub 26 are then retracted, thus tensioning filament member 24 and altering the orientation of flexible tip 40 to a desired configuration. Once the tip configuration is properly altered to retain drainage catheter 20 inside a patient's body cavity, filament member 24 is wrapped around filament accepting region 80. Securing member 28 is then snapped on filament accepting region 80 over filament member 24 to lock the filament member in its tensioned and tip-altering configuration.

Once drainage is complete, one of first segment 62 and second segment 64 is severed, thus permitting filament member 24 to be removed from drainage catheter 20. In particular, while filament member 24 is securely retained within flexible tip 40 by insert member 34, pulling either first segment 62 or second segment 64 after the other segment has been severed slides the entire filament member 24 out of flexible tip 40 and elongated hollow drainage tube 22. The drainage catheter 20 may then be removed from a patient's body, or in the alternative, a stiffening cannula may then be used to facilitate retraction and removal of drainage catheter 20 from a patient's body.

Of course, the present invention is not limited to the specific type of drainage catheter shown in FIGS. 1–7. For instance, and in another embodiment shown in FIGS. 15 and 16, drainage catheter 120 is of the Malecot variety. Drainage catheter 120 comprises elongated hollow drainage tube 122, filament member 124, hub 126 and stiffening cannula 128. Elongated hollow drainage tube 122 includes proximal end 130, distal end 132 and insert member 134. While proximal end 130 is connected to hub 126, distal end 132 includes tip 136, filament routing channel 164, and a series of slots, which define ribs 146, 148, 150 and 152. Like flexible tip 40 of elongated hollow drainage tube 22 of FIGS. 1–6, tip 136 of elongated hollow drainage tube 122 includes fluid opening 154 extending through conical portion 156. However, instead of drainage openings, distal end includes a series of slots which permit ribs 146, 148, 150 and 152 to extend outwardly from elongated hollow drainage tube 122 upon movement of distal end 132 toward proximal end 130, thus forming a drainage opening.

Insert member 134, shown in FIGS. 15 and 16, is positioned in tip 136 of distal end 132, and preferably includes opening 158. Insert member 134 is positioned and retained in flexible tip in much the same way as is described above in relationship to insert member 34—to define filament routing channel 164. Moreover, insert member 134 may also preferably be constructed from the material described in relation to insert member 34 above. Finally, drainage catheter 120 may further include a second insert member (not shown), described above in reference to FIG. 14, to facilitate use of stiffening cannula 128 in combination with drainage catheter 120.

Much like filament member 24, filament member 124 includes a first segment 160 and a second segment 162. Similarly, hub 126 includes sleeve 170, barrel portion 172, a drainage passageway, filament accepting region 176, filament member passageways 178 and 180, and connection region 182. The filament member and hub may be constructed as has been described above, and function in substantially the same manner.

Stiffening cannula 128 is shown as including elongated rod portion 182 and knob 184. Elongated rod portion 182 is designed to extend through the inner portion of elongated hollow drainage tube 122, while knob 184 preferably includes mating threads (not shown) which releasably lock onto connection region 183 of hub 126. Stiffening cannula 128 facilitates insertion of drainage catheter 120 into a patient's body, and ensures proper retraction of distal end 132 and expansion of the distal end ribs. To this end, it will be appreciated that the tip of elongated rod portion may be sharpened to facilitate insertion into a patient's body. Moreover, while shown in FIGS. 15 and 16 as a single rod for purposes of demonstrating the principle of the invention, the stiffening cannula preferably comprises an inner sharpened stylet and an outer hollow cannula. While the stylet is eventually removed from a patient after insertion of the drainage catheter and before expanding of the ribs, the outer hollow cannula preferably remains inside the catheter to facilitate insertion and rib expansion, as would be know by those of ordinary skill in the art with the present disclosure before them.

The Malecot type drainage catheter operates somewhat differently from drainage catheter 20 shown in FIGS. 1–7. As is shown in FIGS. 15 and 16, stiffening cannula 128 is first inserted through elongated hollow drainage tube 122, before knob 184 on stiffening cannula 128 is releasably secured to hub connection region 182 of drainage catheter 120. Reinforced, the drainage catheter 120 is inserted into the body cavity of a patient. Upon proper placement and location of distal end 132 of the drainage catheter into a body cavity and removal of all or a portion of stiffening cannula 128 (depending on whether the stiffening cannula includes separate stylet and cannula components as described above), the portion of first segment 160 and second segment 162 of filament member 124 extending out of hub 126 are pulled away from the hub. Pulling the exposed portions of filament member 124, in turn, tensions the entire filament member and moves distal end 132 of elongated hollow drainage tube 122 toward proximal end 130 thereof. Inasmuch as both the first and second segments of filament member 124 are firmly secured in flexible tip 136 by insert member 134, distal end forces ribs 146, 148, 150 and 152 outwardly to an expanded orientation. Expansion of the ribs, in turn, allows fluid to drain through elongated hollow drainage tube 122, through the drainage passageway in hub 126 and out of the hub—upon removal of stiffening cannula 128. Of course, inasmuch as filament member 124 is retained in a fluid tight manner in filament member passageways 178 and 180, no fluid leaks through hub until the hub drainage passageway is opened for drainage.

A method for forming drainage catheter 20 that is the subject of the present invention is also disclosed. In particular, and as is shown in FIGS. 8–11, filament member 24 is first threaded through opening 48 in insert member 34. As an alternative, filament member 24 may be molded directly into insert member 34, if so desired. Insert member 34 is then placed on mandrel 190, which includes smaller diameter portion 192, larger diameter portion 194 and shoulder 196. As can be seen from FIGS. 8–11, insert member 34 has opening 48 which has an inner diameter sufficient to slide over smaller diameter portion 192 of mandrel, yet which allows insert member 34 to abut shoulder 196 which defines the beginning of larger diameter portion 194.

Once in position and as shown in FIGS. 9 and 10, elongated hollow drainage tube 22 is placed over mandrel such that at least a portion of the elongated hollow drainage tube extends beyond insert member 34. Once in position, and as shown in FIG. 11, elongated hollow drainage tube 22, in combination with mandrel 190, are inserted into forming die 200. Forming die 200 comprises inner molding portion 202, which preferably includes both a conical portion 206 and a cylindrical portion 208. Of course, inner molding portion 202 may take any desired shape corresponding to a desired flexible tip shape. For purposes of this disclosure, flexible tip 40 is formed into a substantially conical shape.

Energizing element 204, shown in FIG. 11, is associated with forming die 200. As is shown, energizing element 204 comprises coil 210 emanating from a energy source 212 and wrapping around forming die 200. Preferably, energy source 212 generates electromagnetic energy in the form of radio frequency energy which heats forming die 200. Of course, it is likewise contemplated that energizing element 204 may comprise other generators of electromagnetic radiation or other forms of direct heat. Such an energizing element may be positioned directly above, surrounding, or inside forming die 200, as would be known by those with ordinary skill in the art with the present with the present disclosure before them.

Before insertion of elongated hollow drainage tube 22 and mandrel 190 into forming die 200, the forming die is heated to a desired flexible tip forming temperature. Pre-heating facilitates insertion of hollow elongated tube 22 into conical portion 206 of forming die 200. Moreover, pre-heating also accelerates formation of the conically shaped flexible tip 40. Inasmuch as insert member 34 is preferably formed of a plastic material somewhat similar to that of the elongated hollow drainage tube 22, insert member 34 is directly molded into flexible tip 40 of elongated hollow drainage tube 22. Preferably, insert member 34 bonds chemically with the elongated hollow drainage tube 22, thus forming filament routing channel 66. Of course, a chemical fusion may also occur if insert member is of the same material as the elongated hollow drainage tube. In the situation where insert member is constructed from a non-plastic material, insert member 34 may simply be molded into flexible tip 40 without a permanent chemical bond.

Forming of insert member 34 into flexible tip 40, in turn, slidably secures filament member 24 in flexible tip 40, with first segment 62 and second segment 64 extending through filament routing channel 66 and into elongated hollow drainage tube 22. Inasmuch as filament member 24 preferably has a substantially higher melting point than that of at least one of insert member 34 or elongated hollow drainage tube 22, the filament member does not bond directly to either the insert member or the elongated hollow drainage tube. Thus, filament member 24 remains slidable within filament routing channel 66 in flexible tip 40, relative to both insert member 34 and elongated hollow drainage tube 22.

Of course, if second insert member 52 is contemplated for use with the present invention, as is shown in FIG. 14, the second insert member may be placed on mandrel 190 before insert member 34, thus forcing a different filament member attachment orientation as described above.

Notably, drainage openings 42 are preferably drilled in elongated hollow drainage tube 22 before formation of flexible tip 40. Pre-drilled prevents inadvertent severing of first segment 62 or second segment 64 of filament member 24 while positioned inside elongated hollow drainage tube 22. Moreover, if a more substantial pigtail or 360° loop in flexible tip 40 is desired, filament member 24 may be pulled from inside elongated hollow drainage tube 22, out of a drainage or other opening, run along an outside portion of elongated hollow drainage tube 22, then inserted back into the tube. The filament may then be extending through the entirety of the elongated hollow drainage tube 22 by a blowing technique, crochet needle or other technique as would be known by those of ordinary skill in the art with the present disclosure before them.

The present method, however, eliminates the need for time-consuming threading of the filament member from the proximal end of the elongated hollow drainage tube, through an opening in the distal end of drainage catheter, back toward the proximal end of the drainage catheter, through another opening reentering the drainage tube, and back all the way down and out the proximal end. In contrast, the filament member is simply positioned within the elongated hollow drainage tube simultaneously with the formation of the distal end and flexible tip.

The foregoing description and drawings merely explain and illustrate the invention and the invention is not limited thereto except insofar as the appended claims are limited as those skilled in the art who have the present disclosure before them will be able to make modifications and variations without departing from the scope of the invention.

What is claimed is:

1. A drainage catheter for draining fluid from a body cavity of a patient, said drainage catheter comprising:

an elongated hollow drainage tube having a proximal end, a distal end, a tip associated with said distal end of said elongated hollow drainage tube, a flexible region substantially adjacent to said tip, and an inner tube surface and an outer tube surface defining a tube wall;

at least one aperture in said distal end of said elongated hollow drainage tube in fluid communication with and into said elongated hollow drainage tube, to facilitate drainage of fluids from a body cavity through said elongated hollow drainage tube;

a hub associated with said proximal end of said elongated hollow drainage tube about said outer tube surface;

a filament routing channel operably positioned within said distal end of said elongated hollow drainage tube; and at least one filament member, having at least two ends, at least a portion of the filament member being operably associated with said distal end of said drainage tube for altering the shape of the flexible region to facilitate retention of at least a portion of the elongated hollow drainage tube inside a patient's body, said at least one filament member reversing direction wholly within at least a portion of said distal end of said drainage tube and extending through at least a portion of said elongated hollow drainage tube and at least one of said at least two ends emanating from at least one of said hub and said proximal end of said elongated hollow drainage tube, at least a portion of said at least one filament member being positioned within said elongated hollow drainage tube and routed through said filament routing channel for slidable movement therethrough such that said at least one filament member is slidably maintained within said distal end of said elongated hollow drainage tube.

2. The drainage catheter according to claim 1 wherein at least a portion of said filament routing channel is positioned in said elongated hollow drainage tube proximate said tip.

3. The drainage catheter according to claim 1 wherein a portion of said at least one filament member is routed through said filament routing channel in the distal end said elongated hollow drainage tube wall, between said inner tube surface and said outer tube surface.

4. The drainage catheter according to claim 1 wherein said at least one filament member includes at least a first segment and a second segment, said first and second segments emanating from said filament routing channel and extending through at least a portion of said elongated hollow drainage tube.

5. The drainage catheter according to claim 1 wherein said hub includes a drainage passageway in communication with said elongated hollow drainage tube to facilitate drainage of fluid from a body cavity to a drainage container.

6. The drainage catheter according to claim 1 wherein at least a portion of said at least one filament member extends outside of said elongated hollow drainage tube to facilitate alteration of the shape of at least a portion of said distal end.

7. The drainage catheter according to claim 1 further including a filament securing member operably associated with at least one end of said filament member to facilitate locking of said distal end in an altered shape to, in turn, enable retention of at least a portion of the elongated hollow drainage tube inside a patient's body.

8. The drainage catheter according to claim 1 wherein said elongated hollow drainage tube further includes at least one drainage opening to facilitate drainage of fluids from a body cavity through said elongated hollow drainage tube.

9. The drainage catheter according to claim 8 wherein said elongated hollow drainage tube further includes at least two drainage openings, and wherein at least a portion of said at least one filament member extends outside of said elongated hollow drainage tube, through and between at least two of said drainage openings, to enhance alteration of the shape of said distal end of said elongated hollow drainage tube.

10. A drainage catheter for draining fluid from a body cavity of a patient, said drainage catheter comprising:

an elongated hollow drainage tube having a proximal end, a distal end, a tip associated with said distal end of said elongated hollow drainage tube, a flexible region substantially adjacent to said tip, and an inner tube surface and an outer tube surface defining a tube wall;

at least one aperture in said distal end of said elongated hollow drainage tube in fluid communication with and into said elongated hollow drainage tube, to facilitate drainage of fluids from a body cavity through said elongated hollow drainage tube;

a hub associated with said proximal end of said elongated hollow drainage tube about said outer tube surface;

a filament routing channel operably positioned within said distal end of said elongated hollow drainage tube; and at least one filament member, having at least two ends, at least a portion of the filament member being operably associated with said distal end of said drainage tube for altering the shape of the flexible region to facilitate retention of at least a portion of the elongated hollow drainage tube inside a patient's body, said at least one filament member extending through at least a portion of said elongated hollow drainage tube and at least one of said at least two ends emanating from at least one of said hub and said proximal end of said elongated hollow drainage tube, at least a portion of said at least one filament member being positioned within said elongated hollow drainage tube and routed through said filament routing channel for slidable movement therethrough such that said at least one filament member is slidably maintained within said distal end of said elongated hollow drainage tube, said at least one filament member being slidably maintained in said distal end of said elongated hollow drainage tube at least in part by at least one insert member.

11. The drainage catheter according to claim 10 wherein the at least one insert member is formed from a metal member suitable to provide a radiopaque marker inside said elongated hollow drainage tube.

12. The drainage catheter according to claim 10 wherein at least a portion of said filament routing channel is positioned between said insert member and said inner tube wall of said elongated hollow drainage tube.

13. The drainage catheter according to claim 10 wherein said at least one insert member is constructed at least in part from a material which is distinct from at least a portion of said elongated hollow drainage tube.

14. The drainage catheter according to claim 13 wherein both said at least one insert member and said elongated drainage tube are constructed from plastic, but wherein the at least one insert member is constructed from a higher durometer plastic than the elongated hollow drainage tube.

15. The drainage catheter according to claim 14 wherein said at least one insert member is chemically bonded within said distal end of said elongated hollow drainage tube to substantially preclude damage to said filament routing channel by slidable movement of said at least one filament member therethrough.

16. The drainage catheter according to claim 14 wherein the at least one insert member has a higher melting point than the elongated hollow drainage tube.

17. The drainage catheter according to claim 10 wherein said at least one filament member is slidably retained in said distal end of said elongated hollow drainage tube at least in part by said at least one insert member to define an orientation of said filament member relative to said inner surface of said elongated hollow drainage tube, and wherein said filament member is further slidably retained in said distal end of said elongated hollow tube at least in part by a second insert member, said second insert member altering the orientation of the filament member relative to the inside surface of said elongated hollow drainage tube.

18. A drainage catheter for draining fluid from a body cavity of a patient, said drainage catheter comprising:
- an elongated hollow drainage tube having a proximal end, a distal end and a tip associated with said distal end of said elongated hollow drainage tube, a flexible region substantially adjacent said tip, and an inner tube surface and an outer tube surface defining a tube wall;
- at least one aperture in said distal end of said elongated hollow drainage tube in fluid communication with and into said elongated hollow drainage tube, to facilitate drainage of fluids from a body cavity through said elongated hollow drainage tube;
- a hub associated with said proximal end of said elongated hollow drainage tube about said outer tube surface, said hub including a drainage passageway communicating with said elongated hollow drainage tube and a barrel portion;
- at least one filament member operably associated with said distal end of said drainage tube for altering the shape of the flexible region to facilitate retention of at least a portion of the elongated hollow drainage tube inside a patient's body, said at least one filament member extending through at least a portion of said elongated hollow drainage tube, into said hub drainage passageway and emanating from said hub;
- said hub having a single unitary construction and further including at least one continuous filament member passageway extending through at least one entire side of said hub, said at least one filament member passageway being shaped to accommodate only the at least one filament member, without obstruction by further sealing members, through said at least one entire side of said hub; and
- said at least one filament member passageway further enabling slidable movement of said filament member therethrough, yet maintaining a substantially liquid tight seal between said drainage passageway and said hub barrel.

19. The drainage catheter according to claim 18 wherein said at least one filament member is slidably retained in a filament routing channel operably positioned in said distal end of said drainage tube.

20. The drainage catheter according to claim 18 wherein said at least one filament member includes at least a first segment and a second segment, each of said first and second segments emanating through a filament member passageway in said hub.

21. A drainage catheter for draining fluid from a body cavity of a patient, said drainage catheter comprising:
- an elongated hollow drainage tube having a proximal end, a distal end and a tip associated with said distal end of said elongated hollow drainage tube, a flexible region substantially adjacent said tip, and an inner tube surface and an outer tube surface defining a tube wall;
- at least one aperture in said distal end of said elongated hollow drainage tube in fluid communication with and into said elongated hollow drainage tube, to facilitate drainage of fluids from a body cavity through said elongated hollow drainage tube;
- a hub associated with said proximal end of said elongated hollow drainage tube about said outer tube surface, said hub including a drainage passageway communicating with said elongated hollow drainage tube and a barrel portion;
- at least one filament member operably associated with said distal end of said drainage tube for altering the shape of the flexible region to facilitate retention of at least a portion of the elongated hollow drainage tube inside a patient's body, said at least one filament member extending through at least a portion of said elongated hollow drainage tube, into said hub drainage passageway and emanating from said hub; and
- said hub further including at least one filament member passageway extending through said hub, said at least one filament member passageway enabling slidable movement of said filament member therethrough, yet maintaining a substantially liquid tight seal between said drainage passageway and said hub barrel,
- said at least one filament member being slidably retained in a filament routing channel operably positioned in said distal end of said drainage tube, and
- said at least one filament member being slidably retained in said distal end of said elongated hollow drainage tube at least in part by at least one insert member, which defines at least a portion of said filament routing channel.

22. A drainage catheter for draining fluid from a body cavity of a patient, said drainage catheter comprising:
- an elongated hollow drainage tube having a proximal end, a distal end and a tip associated with said distal end of said elongated hollow drainage tube, a flexible region substantially adjacent said tip, and an inner tube surface and an outer tube surface defining a tube wall;
- at least one aperture in said distal end of said elongated hollow drainage tube in fluid communication with and into said elongated hollow drainage tube, to facilitate drainage of fluids from a body cavity through said elongated hollow drainage tube;
- a hub associated with said proximal end of said elongated hollow drainage tube about said outer tube surface, said hub including a drainage passageway communicating with said elongated hollow drainage tube and a barrel portion;
- at least one filament member operably associated with said distal end of said drainage tube for altering the shape of the flexible region to facilitate retention of at least a portion of the elongated hollow drainage tube inside a patient's body, said at least one filament member extending through at least a portion of said elongated hollow drainage tube, into said hub drainage passageway and emanating from said hub; and
- said hub further including at least one filament member passageway extending through said hub, said at least one filament member passageway enabling slidable movement of said filament member therethrough, yet maintaining a substantially liquid tight seal between said drainage passageway and said hub barrel,
- said hub having a melting point lower than the melting point of said at least one filament member.

23. A method for forming a drainage catheter, said method comprising the steps of:
- providing an elongated hollow drainage tube having a proximal end, a distal end, a tip associated with said distal end of said elongated hollow drainage tube, a flexible region substantially adjacent said tip, and an inner tube surface and an outer tube surface defining a tube wall;
- positioning at least one filament member, said at least one filament member having at least two ends, inside said distal end of said elongated hollow drainage tube;

heating at least a portion of said distal end of said elongated hollow drainage tube to form a filament routing channel positioned within said distal end, said at least one filament member being positioned within and routed through said filament routing channel such that said at least one filament member is slidably maintained within said distal end of said elongated hollow drainage tube;

running said filament member through at least a portion of said elongated hollow drainage tube, such that said filament member emanates from the proximal end of said elongated hollow drainage tube; and forming a hub on the proximal end of said elongated hollow drainage tube.

24. The method according to claim 23 wherein the step of heating at least a portion of said distal end of said elongated hollow drainage tube to form a filament routing channel positioned within said distal end further includes heating at least a portion of said distal end of said elongated hollow drainage tube proximate said at least one insert member such that said at least one insert member is secured within said elongated hollow drainage tube to form said filament routing channel, thus slidably retaining said at least one filament member at least partially within said filament routing channel within said distal end of said elongated hollow drainage tube.

25. The method according to claim 23 wherein step of positioning the at least one insert member and at least one filament member inside the distal end of said elongated hollow drainage tube further includes the steps of:

positioning said at least one insert member on a mandrel, said mandrel including a smaller diameter portion and a larger diameter portion, such that said at least one insert member rests on said smaller diameter portion, and placing said elongated hollow drainage tube over said at least one insert member and said at least one filament member, such that said at least one insert member is inside the distal end of said elongated hollow drainage tube and said at least one filament member runs inside at least a portion of said elongated hollow drainage tube.

26. The method according to claim 23 further including the step of associating said at least one filament member with at least one insert member before the step of positioning the at least one filament member inside said distal end of said elongated hollow drainage tube.

27. The method according to claim 26 wherein the step of positioning the at least one filament member inside said distal end of said elongated hollow drainage tube further includes orienting said at least one insert member and said at least one filament member inside said distal end of said elongated hollow drainage tube.

28. The method according to claim 27 wherein the step of orienting said at least one insert member and said at least one filament member inside the distal end of said elongated hollow drainage tube provides the at least one filament member with an orientation relative to the inside surface of said elongated hollow drainage tube, and wherein the method further includes the step of positioning said at least one filament member relative to a second insert member inside said distal end of said elongated hollow drainage tube to alter the orientation of the filament member relative to the inside surface of the elongated hollow drainage tube.

29. The method according to claim 23 further including the step of drilling at least one drainage opening in said elongated hollow drainage tube.

30. The method according to claim 29 wherein the step of drilling at least one drainage opening in said elongated hollow drainage tube occurs before the step of positioning said filament member inside said distal end of said elongated hollow drainage tube.

31. The method according to claim 23 further including the step of forming at least a portion of said distal end of said elongated hollow drainage tube to a desired shape.

32. The method according to claim 31 wherein the step of forming at least a portion of said distal end of said elongated hollow drainage tube to a desired shape occurs substantially simultaneously with the step of heating at least a portion of said distal end of said elongated hollow drainage tube.

33. The method according to claim 31 wherein the step of forming the distal end of said elongated hollow drainage tube to a desired shape includes inserting the distal end of said elongated hollow drainage tube into a die.

34. The method according to claim 33 wherein the step of energizing includes applying electromagnetic energy to at least a portion of said distal end of said elongated hollow drainage tube.

35. The method according to claim 34 wherein the step of energizing further includes applying electromagnetic energy to a forming die, which, in turn, transmits heat to at least a portion of said distal end of said elongated hollow drainage tube.

36. A method for forming a drainage catheter, said method comprising the steps of:

providing an elongated hollow drainage tube having a proximal end, a distal end, a tip associated with said distal end of said elongated hollow drainage tube, a flexible region substantially adjacent said tip, and an inner tube surface and an outer tube surface defining a tube wall;

associating at least one filament member, having at least two ends, with the distal end of the elongated hollow drainage tube to facilitate alteration of the shape of the flexible region to facilitate retention of at least a portion of the elongated hollow drainage tube inside a patient's body;

running said at least one filament member through at least a portion of said elongated hollow drainage tube, such that said at least one filament member emanates from the proximal end of said elongated hollow drainage tube;

forming a hub, said hub including a drainage passageway and a barrel having a single unitary construction, onto said proximal end of said elongated hollow drainage tube and directly around said at least one filament member, thereby creating at least one filament member passageway extending through said hub to house said at least one filament member, said at least one filament member passageway being shaped to accommodate only the at least one filament member, without obstruction by further sealing members, through said at least one entire side of said hub.

37. The method according to claim 36 wherein said at least one filament member includes at least a first segment and a second segment, such that the step of forming a hub includes creating a filament member passageway in association with each of said first and second segments, thus enabling each of said first and second filament member segments to extend through a distinct filament passageway in said hub.

38. A method for forming a drainage catheter, said method comprising the steps of:

providing an elongated hollow drainage tube having a proximal end, a distal end, a tip associated with said distal end of said elongated hollow drainage tube, a flexible region substantially adjacent said tip, and an inner tube surface and an outer tube surface defining a tube wall;

associating at least one filament member, having at least two ends, with the distal end of the elongated hollow drainage tube to facilitate alteration of the shape of the flexible region to facilitate retention of at least a portion of the elongated hollow drainage tube inside a patient's body;

running said at least one filament member through at least a portion of said elongated hollow drainage tube, such that said at least one filament member emanates from the proximal end of said elongated hollow drainage tube;

forming a hub, said hub including a drainage passageway and a barrel, onto said proximal end of said elongated hollow drainage tube and directly around said at least one filament member, thereby creating at least one filament member passageway extending through said hub to house said at least one filament member;

cooling and thus at least partially shrinking the at least one filament member passageway around at least a portion of said at least one filament member creating a fluid tight seal between said drainage passageway and hub barrel, yet enabling slidable movement of said at least one filament member relative to said hub.

* * * * *